United States Patent [19]
Wong et al.

[11] Patent Number: 5,705,194
[45] Date of Patent: *Jan. 6, 1998

[54] PHARMACEUTICAL COMPOSITIONS CONTAINING POLYALKYLENE BLOCK COPOLYMERS WHICH GEL AT PHYSIOLOGICAL TEMPERATURE

[75] Inventors: Sui-Ming Wong, Collegeville; Eugene R. Cooper, Berwyn; Shuqian Xu, Exton, all of Pa.

[73] Assignee: NanoSystems L.L.C., King of Prussia, Pa.

[*] Notice: The term of this patent shall not extend beyond the expiration date of Pat. No. 5,565,188.

[21] Appl. No.: 727,863

[22] Filed: Oct. 8, 1996

Related U.S. Application Data

[63] Continuation-in-part of Ser. No. 393,972, Feb. 24, 1995, Pat. No. 5,565,188.

[51] Int. Cl.⁶ .............................. A61K 7/06; A61K 7/135
[52] U.S. Cl. .................... 424/489; 424/9.411; 424/9.4; 424/495; 424/499; 514/718; 514/975
[58] Field of Search .................... 424/9.411, 9.4, 424/9.45, 489, 495, 499; 514/718, 975

[56] References Cited

U.S. PATENT DOCUMENTS

| | | | |
|---|---|---|---|
| 3,740,421 | 6/1973 | Schmolka | 424/65 |
| 3,867,533 | 2/1975 | Schmolka | 424/258 |
| 4,465,663 | 8/1984 | Schmolka | 424/62 |
| 4,587,365 | 5/1986 | Anchor | 568/619 |

OTHER PUBLICATIONS

Chemical Abstracts 117:151640, "High Molecular Weight Polyetherpolyols".

*Primary Examiner*—Frederick Krass
*Attorney, Agent, or Firm*—McDermott, Will & Emery

[57] ABSTRACT

There is disclosed a pharmaceutical composition which gels at physiological temperature. The composition is comprised of a block copolymer containing one or more polyoxyethylene blocks and one or more polyoxy (higher alkylene) blocks wherein at least some of the blocks are linked together by a linking group characterised in that the linking group is an oxymethylene group, and a therapeutic agent. The therapeutic agent is present as (i) nanoparticles of the therapeutic agent having the block copolymer adsorbed on the surface thereof, (ii) a suspension in a solution of the block copolymer, or (iii) as an aqueous solution in a solution of the block copolymer.

7 Claims, No Drawings

PHARMACEUTICAL COMPOSITIONS CONTAINING POLYALKYLENE BLOCK COPOLYMERS WHICH GEL AT PHYSIOLOGICAL TEMPERATURE

RELATIONSHIP TO OTHER APPLICATIONS

This is a continuation-in-part of U.S. Ser. No. 08/393,972, filed Feb. 24, 1995, now, U.S. Pat. No. 5,565,188, issued Oct. 15, 1996.

FIELD OF THE INVENTION

The present invention is directed to pharmaceutical compositions containing a therapeutic agent and a polyalkylene block copolymer which gels at physiological temperature.

BACKGROUND OF INVENTION

Bioavailability is the degree to which a therapeutic agent becomes available to the target tissue after administration.

Many factors can affect bioavailability including the dosage form and various properties, e.g., dissolution rate of the therapeutic agent, amount of time the therapeutic agent is exposed to the desired site.

Therapeutic agents, ranging from poorly to highly soluble in water, can be administered more effectively if the therapeutic agent is able to be delivered and maintained at the site where its therapeutic effect is desired.

U.S. Pat. No. 4,534,959, there is described a composition in an aerosol container. When sprayed the composition gels on the surface of living tissue. This composition contains a polyoxyethylene-polyoxypropylene copolymer. However the copolymer must be present in high percentage. Further, the therapeutic agent must be solubilized. U.S. Pat. No. 3,867,533 relates to another aqueous gel composition; U.S. Pat. No. 4,465,663 is similar and relates to cosmetic gels.

SUMMARY OF THE INVENTION

In accordance with the present invention there is provided a pharmaceutical composition which gels at physiological temperatures and which is comprised of a) block copolymer containing one or more polyoxyethylene blocks and one or more polyoxy(higher alkylene) blocks wherein at least some of the blocks are linked together by a linking group characterized in that the linking group is an oxymethylene group, and b) a therapeutic agent, wherein the therapeutic agent is present as
(I) nanoparticles of the therapeutic agent having the block copolymer adsorbed on the surface thereof,
(II) a suspension in a solution of the block copolymer, or
(III) as an aqueous solution in a solution of the block copolymer.

DESCRIPTION OF PREFERRED EMBODIMENTS

The Block Copolymer—The Gelling Agent

The block copolymer contains one or more polyoxyethylene blocks and one or more polyoxy (higher alkylene) blocks wherein at least some of the blocks are linked together by a linking group characterized in that the linking group is an oxymethylene group.

Preferred copolymers of the invention include those wherein the polyoxy (higher alkylene) blocks are selected from polyoxypropylene and polyoxybutylene blocks.

In one embodiment, block copolymers are provided having the following repeating units in random order

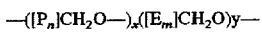

wherein
P is oxypropylene;
E is oxyethylene;
n is an integer from 2 to 70, preferably from 4 to 20;
m is an integer from 2 to 250, preferably from 9 to 20;
x is an integer from 1 to 100, preferably from 1 to 10; and,
y is an integer from 1 to 100, preferably from 1 to 50.

In a preferred embodiment block copolymers are used having the following repeating units in random order:

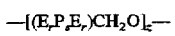

wherein
P is oxypropylene;
E is oxyethylene;
r is an integer from 2 to 160, preferably from 75 to 150;
s is an integer from 15 to 65, preferably from 30 to 50; and,
z is an integer from 2 to 50, preferably from 2 to 10.

In a particularly preferred embodiment block copolymers are used having the following repeating units in random order:

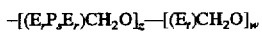

wherein
P is oxypropylene;
E is oxyethylene;
r is an integer from 2 to 160, preferably from 75 to 150, most preferably 141;
s is an integer from 15 to 65, preferably from 30 to 50, most preferably 44;
z is an integer from 2 to 50, preferably from 2 to 10, most preferably 4 to 8;
t is an integer from 1 to 10, preferably from 1 to 3, most preferably 1; and
w is an integer from 2 to 50, preferably from 2 to 10, most preferably 4 to 8.

The molecular weight of a block copolymer as measured by gel permeation chromatography against poly (oxyethylene) standards may range from 10,000 to 500,000, preferably from 50,000 to 250,000.

The polymers can be prepared by a process wherein one or more dihydroxy terminated polymers selected from poly (ethylene glycol), poly (higher alkylene glycol) and block copolymers thereof are reacted in solution with a dihalomethane in the presence of a base.

Examples of suitable solvents in which the reagents can be dissolved include dihalomethanes and other known organic solvents such as benzene, chlorobenzene and toluene or mixtures thereof.

Preferably, an excess of the dihalomethane reagent is used as the solvent. Even though the dihalomethane is used in an amount which can far exceed the stoichiometric amount needed to couple with the polymeric reactants, products of high molecular weight can still be achieved.

Although any dihalomethane or mixture thereof may be used such as dichloromethane, dibromomethane or diiodomethane, the preferred dihalomethane is dichloromethane.

The required alkaline reaction conditions may be obtained by incorporating one or more bases such as sodium hydroxide and potassium hydroxide.

Examples of the dihydroxy terminated polymer starting materials include the polyethylene glycols (PEGs) and the polypropylene glycols (PPGs) which are available commercially. Specific examples include PEG 400, PEG 6000 and PPG 1000 for which the number associated with the name "PEG" or "PPG" indicates the average molecular weight of the polymer and is proportional to the average number of repeating oxyethylene or oxypropylene units in the polymer. Preferred polyalkylene glycols have molecular weights ranging from 200 to 10,000 and particularly PEG 6000.

Further examples of the dihydroxy terminated polymer starting materials include the dihydroxy terminated E—P—E triblock copolymers of poly(oxyethylene) (E) and poly(oxypropylene) (P) which are commercially available in the form of Pluronic™ surfactants. These starting materials provide the "(E,P,E,)" portion of the block copolymers defined above. Preferred triblock copolymers have molecular weights ranging from 4,000 to 15,000. Particular Pluronic™ surfactants that can be used as starting materials include F108, F68, F127 and L6000 and particularly-F108. Triblock copolymers derived from F108, which has longer chain lengths of propyleneoxy groups, provide better hydrophobic interactions with the therapeutic or diagnostic agent particles. This provides better size reduction of particles. Further, F108 has a gel point very close to physiological temperature at low concentrations. F108 corresponds to the "(E,P,E,)" portion r is 141 and s is 44.

The copolymers contain both hydrophilic polyoxyethylene blocks and hydrophobic polyoxy (higher alkylene) blocks. The balance between the hydrophilicity and hydrophobicity of the copolymers can be adjusted by appropriate choice of starting materials to give the optimum physical and chemical characteristics required.

The currently preferred block copolymer has the formula:

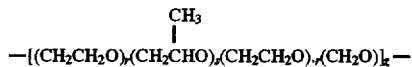

wherein r is 141; s is 44 and z is 3 to 4.

The block copolymers that are useful in the present invention have desirable rehological properties for use in therapeutic and diagnostic compositions. At concentrations as low as 2.5% w/v in phosphate balance salt solution (PBS) or in water, particular examples of the described block copolymers have gel points close to physiological temperature (37.4° C.). The viscosity of these block copolymers at 3.5% and 5.5% in PBS change abruptly from less than 20 cps at room temperature to more than 1500 cps at physiological temperature while the pH and osmolality of the block copolymer solutions remain comparable to PBS. Thus, compositions containing these block copolymers can be administered (e.g. subcutaniously or orally) as low viscosity compositions at room temperature and, when they reach physiological temperature, will tend to gel.

Because of these and other properties, the described block copolymers are useful as bioadhesives and/or control release agents for the delivery of therapeutic or diagnostic agents to the eye, ear, pulmonary systems, biocavity and gastrointestinal tract.

Therapeutic or Diagnostic Agents

Suitable therapeutic or diagnostic agents useful in the three types of formulations used in the present invention (i.e., nanoparticles, solutions and suspensions) be selected from a variety of known classes of therapeutic or diagnostic agents including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radio- pharmaceuticals, sex hormones (including steroids), anti-allergic agents, stimulants and anoretics, sympathomimetics, thyroid agents, vasodilators and xanthines. Preferred therapeutic or diagnostic agents include those intended for oral administration, topically, ophalmic and nasal application. A description of these classes of therapeutic agents and diagnostic agents and a listing of species within each class can be found in Martindale, The Extra Pharmacopoeia, Twenty-ninth Edition, The Pharmaceutical Press, London, 1989. The therapeutic or diagnostic agents are commercially available and/or can be prepared by techniques known in the art.

Solutions and Suspensions

The pharmaceutical compositions of the present invention can be applied to known drugs in nasal, oral and ophthalmic solutions and suspensions to produce an increase in sustained drug release, increase in drug residence time or to enhanced bioavailability.

The present block copolymers are particularly useful with therapeutic agents for the treatment of the eyes such as the following:

A. for ophthalmic solution application—acetylcholine chloride, atropine sulfate, benoxinate hydrochloride, carbachol, chloramphenicol, chymotrypsin, cromolyn sodium, cyclopentolate hydrochloride, demecarium bromide, dexamethasone sodium phosphate, neomycin sulfate, dipivefrin hydrochloride, echolthiophate iodide, epinephrine, epinephrine bitartrate, epinephryl borate, eucatropine hydrochloride, flurbiprofen sodium, gentamicin sulfate, glycerin, gramicidin, polymyxin B sulfates, homatropine hydrobromide, hydroxyamphetamine hydrobromide, hydroxypropyl methylcellulose, hydrocorticone, idoxuridine, levobunolol hydrochloride, naphazoline hydrochloride, neomycin, gramicidin, oxymetazoline hydrochloride, phenylephrine hydrochloride, phystigmine salicylate, pilocarpine hydrochloride, pilocarpine nitrate, prednisolone sodium phosphate, proparacaine hydrochloride, scopolamine hydrobromide, sulfacetamide sodium, sulfisoxazole diolamine, tetracaine hydrochloride, tetrahydrozoline hydrochloride, timolol maleate, tobramycin, tropicamide and any of their combinations.

B. for ophthalmic suspension application— chloramphenicol, dexamethaxone, neomycin, fluorometholone, hydrocortisone acetate, hydrocortisone, medrysone, natamycin, prenisolone acetate, oxyteracycline hydrochloride, polymyxin B, sulfacetamide sodium, tetracycline hydrochloride and any of their combinations The present block copolymers are also particularly useful with therapeutic agents for the nasal application such as the following: cromolyn sodium, cyclopentamine hydrochloride, ephedrine sulfate, ephinephrine, flunisolide, lypressin, naphazoline hydrochloride, oxymetazoline hydrochloride, oxytocin, phyenylephrine hydrochloride, tetrahydrozoline hydrochloride and xylometazoline.

The present block copolymers are also particularly useful with therapeutic agents in solutions and suspensions for oral application such as the following: A- oral solutions—acetaminophen, aminobenzoate, aminophylline, amprolium, aspirin, carphenzaine maleate, chloramphenicol, clindamycin palmirate hydrochloride, cloxacillin sodium, cloxacillin sodium, cyanocobalamin Co, cyclosprine, dihydrotachysterol, diphenoxylate hydrochloride, atropine sulfate, doxepine hydrochloride, ergocalciferol, ergoloid mesylates, fluphenzaine hydrochloride, glycerin, guaifenesin, theophyline, haloperidol, hyoscyamine sulfate, isosorbide, levocarnitine, mesoridazine besylate, methadone hydrochloride, methenamine mandelate, metoclopramide, nafcillin sodium, neomycin sulfate, nortriptyline hydrochloride, oxacillin sodium, oxycocone hydrochloride, paramethadione, penicillin G potassium, perphenazine, prednisone, prochlorperazine edisulate, promazine hydrochloride, theophylline, guaifenesin, thioridazine hydrochloride, thiothixene hydrochloride, trimethadione, vancomycin hydrochloride and any of their combinations B-for oral suspensions—acetopminophen, alumina, magnesia, simethicone, amoxicillin, amphotericin B, ampicillin, bacampicillinhydrochloride, bephenium hydroxynaphthoate, cefaclor, cefadroxil, cephalexin, cephradine, chloramphenicol palmitate, chlorothiazide, chlorprothixene, chlestyramine, clavulanate potassium, colestipol hydrochloride, colistin sulfate, cyclacillin, demeclocycline, diazoxide, dicloxacillin sodium, doxycycline, doxycycline calcium, erythromycin estolate, erythromycin ethylsuccinate, erythromycin stearate, erythromycin ethylsuccinate, furazolidone, griseofulvin, hetacillin, hydrocortisone cypionate, hydroxyzine pamoate, ipodate calcium, levopropoxyphene napsylate, mgaldrate, magnesium carbonate, magnesium trisilicate, meprobamtate, methacycline hydrochloride, methamine mandelate, methyldopa, minocycline hydrochloride, nalidixic acid, nitrofurantoin, novobiocin calcium, nystatin, oxytetracycline calcium, penicillin G benzathine, penicillin V, penicillin V benzathine, phenytoin, primidone, probenecid, propoxyphene napsylate, psyllium hydrophilic mucilloid, pyrantel pamoate, pyrvinium pamoate, sulfamethizole, sulfamethoxazole, sulfisoxazole acetyl, tetracycline, thiabendazole, thioridazine, triflupromazine, trimethoprim, trisulfapyrimidines, troleandomycin and any of their combinations.

Nanoparticles

The present invention also has utility to administer and stablize nanoparticles wherein the copolymer is absorbed on the surface of the nanoparticles.

Nanoparticles, described in U.S. Pat. No. 5,145,684, are particles consisting of a poorly soluble therapeutic or diagnostic agent onto which are adsorbed a non-crosslinked surface modifier, and which have an average particle size of less than about 400 nanometers (nm). These nanoparticles provide for increased bioavailability and for improved diagnostic characteristics compared to other materials having larger sizes.

The nanoparticles can comprise a wide variety of therapeutic or diagnostic agents. (Therapeutic agents are sometimes referred to as drugs or pharmaceuticals. The diagnostic agent referred to is typically a contrast agent such as an x-ray contrast agent but can also be other diagnostic materials.) The therapeutic or diagnostic agent exists as a discrete, crystalline phase. The crystalline phase differs from a non-crystalline or amorphous phase which results from precipitation techniques, such as described in EPO 275,796.

The therapeutic or diagnostic agent preferably is present in an essentially pure form. The therapeutic or diagnostic agent must be poorly soluble and dispersible in at least one liquid medium. By "poorly soluble" it is meant that the therapeutic or diagnostic agent has a solubility in the liquid dispersion medium of less than about 10 mg/ml, and preferably of less than about 1 mg/ml. A preferred liquid dispersion medium is water. However, the invention can be practiced with other liquid media in which a therapeutic or diagnostic agent is poorly soluble and dispersible including, for example, aqueous salt solutions, safflower oil and solvents such as ethanol, t-butanol, hexane and glycol. The pH of the aqueous dispersion media can be adjusted by techniques known in the art.

The described block copolymers can be used with NSAIDS. Surface modified nanoparticles comprising an NSAID, e.g., naproxen, demonstrate reduced gastric irritation and/or a more rapid onset of action following oral administration.

Useful NSAIDs can be selected from suitable acidic and nonacidic compounds. Suitable acidic compounds include carboxylic acids and enolic acids. Suitable nonacidic compounds include, for example, nabumetone, tiaramide, proquazone, bufexamac, flumizole, epirazole, tinoridine, timegadine and dapsone.

Suitable carboxylic acid NSAIDs include, for example, salicylic acids and esters thereof, such as aspirin, diflunisal, benorylate and fosfosal; acetic acids, including phenylacetic acids such as diclofenac, alclofenac and fenclofenac, and carbo- and heterocyclic acetic acids such as etodolac, indomethacin, sulindac, rolmerin, fentiazac and tilomisole; propionic acids, such as carprofen, fenbufen, flurbiprofen, ketoprofen, oxaprozin, suprofen, tiaprofenic acid, ibuprofen, naproxen, fenoprofen, indoprofen, pirprofen; and fenamic acids, such as flufenamic, mefenamic, meclofenamic and niflumic.

Suitable enolic acid NSAIDs include, for example, pyrazolones such as oxyphenbutazone, phenylbutazone, apazone and feprazone, and oxicams such as piroxicam, sudoxicam, isoxicam and tenoxicam.

The described nanoparticles can be prepared in accordance with methods disclosed in the prior including U.S. Pat. No. 5,145,684 which is incorporated by reference herein in. The method of the reference comprises the steps of dispersing a therapeutic or diagnostic agent in a liquid dispersion medium and applying mechanical means in the presence of grinding media to reduce the particle size of the therapeutic or diagnostic agent to an effective average particle size of less than about 400 nm. The particles can be reduced in size in the presence of the copolymer. Alternatively, the particles can be contacted with the copolymer surface modifier after attrition.

The therapeutic or diagnostic agent selected is obtained commercially and/or prepared by techniques known in the art in a conventional coarse form. It is preferred, but not essential, that the particle size of the coarse therapeutic or diagnostic agent selected be less than about 100 μm as determined by sieve analysis. If the coarse particle size of the therapeutic or diagnostic agent is greater than about 100 μm, then it is preferred that the particles of the therapeutic or diagnostic agent be reduced in size to less than 100 μm using a conventional milling method such as airjet or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). It is preferred, but not essential, that the block copolymer be present in the premix. The concentration of the block copolymer can vary from about 0.1 to about 90%, and preferably is 1–75%, more preferably 20–60%, by weight based on the total combined weight of the therapeutic or diagnostic agent and surface modifier. The apparent viscosity of the premix suspension is preferably less than about 1000 centipoise.

The premix can be used directly by subjecting it to mechanical means to reduce the average particle size in the dispersion to less than 400 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the therapeutic or diagnostic agent conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

Preparation Conditions for Nanoparticles

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the therapeutic or diagnostic agent. Processing temperatures of less than about 25°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Control of the temperature, e.g., by jacketing or immersion of the milling chamber in ice water are contemplated. Processing pressures from about 1 psi (0.07 kg/cm$^2$) up to about 50 psi (3.5 kg/cm$^2$) are contemplated. Processing pressures from about 10 psi (0.7 kg/cm$^2$) to about 20 psi (1.4 kg/cm$^2$) are typical.

The block copolymer, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

After attrition is completed, the grinding media is separated from the milled particulate product (in either a dry or liquid dispersion form) using conventional separation techniques, such as by filtration, sieving through a mesh screen, and the like.

Particle Size

As used herein, particle size refers to a number average particle size as measured by conventional particle size measuring techniques well known to those skilled in the art, such as sedimentation field flow fractionation, photon correlation spectroscopy, or disk centrifugation. When photon correlation spectroscopy (PCS) is used as the method of particle sizing the average particle diameter is the Z-average particle diameter known to those skilled in the art. By "an effective average particle size of less than about 400 nm" it is meant that at least 90% of the particles have a weight average particle size of less than about 400 nm when measured by the above-noted techniques. In preferred embodiments, the effective average particle size is less than about 300 nm and more preferably less than about 250 nm. In some embodiments, an effective average particle size of less than about 100 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

Liquid Forms

Liquid dosage forms for administration of the present invention include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Topical Forms

Dosage forms for topical administration, including opthalmic, of the present invention include solutions, sprays and inhalants. The active component is admixed under sterile conditions with a physiologically acceptable carrier and any preservatives, buffers or propellants as may be required.

Dosage Levels

Actual dosage levels of active ingredients in the compositions may be varied so as to obtain an amount of active ingredient that is effective to obtain a desired therapeutic or diagnostic response for a particular composition and method of administration. The selected dosage level therefore depends upon the desired therapeutic or diagnostic effect, on the route of administration, on the desired duration of treatment and other factors.

The total daily dose administered to a host in single or divided dose may be in amounts, for example, of from about 1 nanomol to about 5 micromoles per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other therapeutic agents and the severity of the particular disease being treated.

Additives

Besides such inert diluents, the composition can also include buffers, adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonire, agar-agar and tragacanth, or mixtures of these substances, and the like.

These compositions may also contain adjuvants such as preserving, wetting, emulsifying, and dispensing agents. Prevention of the action of microorganisms can be measured by various antibacterial and antifungal agents, for example, parabens, chlorobutanol, phenol, sorbic acid, and the like. It may also be desirable to include isotonic agents, for example sugars, sodium chloride and the like. Prolonged absorption of the pharmaceutical form can be brought about by the use of agents delaying absorption, for example, aluminum monostearate and gelatin.

Method of Treating

A method of treating or diagnosing a mammal comprises the step of administering to the mammal in need of treatment an effective amount of the above-described therapeutic or diagnostic agent composition. The selected dosage level of the therapeutic or diagnostic agent for treatment is effective to obtain a desired therapeutic or diagnostic response for a particular composition and method of administration. The selected dosage level therefore, depends upon the particular therapeutic or diagnostic agent, the desired therapeutic or diagnostic effect, on the route of administration, on the desired duration of treatment and other factors.

It is contemplated that the therapeutic or diagnostic compositions will be particularly useful in oral, subcutaneous, topical, ophthalmic and nasal administration applications. It is expected that even poorly water soluble therapeutic or diagnostic agents may be administered safely. Additionally, therapeutic or diagnostic agents which could not have been administered orally due to poor bioavailability may now be effectively administered.

The following Preparation illustrates the preparation of a block polymer that is useful in the present invention.

Preparation of the Preferred Copolymer

First Preparation

An oxymethylene linked, multiblock copolymer was prepared by the reaction of an $E_{141}P_{44}E_{141}$ triblock copolymer of poly(oxyethylene) ($E_{141}$) and poly(oxypropylene) ($P_{44}$), having an average molecular weight of 14,500, (Pluronic™ 108) with dichloromethane in the presence of potassium hydroxide.

Finely ground potassium hydroxide (66 g) was mixed with dichloromethane (300 mL) under a nitrogen atmosphere at room temperature in a one liter resin kettle equipped with a condenser and a mechanical stirrer. To this was added the triblock copolymer (100 g) dispersed in dichloromethane (700 mL).

The whole was stirred for approximately two hours, then additional dichloromethane (500 mL) was added to reduce the viscosity of the polymer solution. The solution was filtered through a pad of Celite™ (Kieselguhr) and then rotary evaporated under vacuum to give a polymer.

The polymer was characterised by gel permeation chromatography (GPC). Dimethyl formamide (DMF) eluant and styragel columns were employed, calibrated with poly(oxyethylene) standards. Molecular weights and molecular weight distributions were obtained from the GPC curve by reference to this calibration. The preparation was repeated three times with average molecular weights ranging 50,824 to 68,092. The gel point at 4% concentration ranged from 33° to 36° C.

Second Preparation

A block polymer having the structure as follows was prepared.

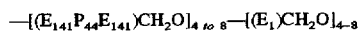

wherein

P is oxypropylene; and

E is oxyethylene.

Pluronic™ F108, as used in the first preparation, and polyethylene glycol (PEG6000- 50 g) were dissolved in dichloromethane and added rapidly to a stirred suspension of powdered sodium hydroxide (100 g) in dichloromethane (275 mL) and stirred under nitrogen for 15-18 hours. The mixture was diluted with dichloromethane (1200 mL), allowed to settle and filtered through a Celite pad to remove inorganics. The solvent is then evaporated.

The product polymer has an average molecular weight of about 143,000, based on the average of three preparation batches, and a gel point of 37° C. (4% concentration in deionized water.

Example 1: Solution for Ophthalmic, Nasal and Oral Application:

3% w/w (however, 1% to 6% may be used, and preferable 2% to 3%) of the most preferred copolymer of the above Second Preparation, is added to commercial products of cromolyn sodium for nasal application, acetylcholine chloride for ophthalmic application and vanomycin for oral application.

The mixtures are allowed to stirred at room temperature overnight in a sanitized area followed by filtration through a 0.2 micron filter.

When the solutions are administered to the eye, to the nose or orally, they form a gel.

Example 2: Suspension for Ophthalmic Application:

A suspension of chloramphenicol is subjected to centrifugation at 15,000g in a close sterile centrifugation container. The supernatant and the drug pellet are collected aseptically in a laminar flow hood. To the supernatant, 4% of the preferred copolymer of the above Second Preparation, is added (however, 1% to 6%, preferably 3% to 5% w/w may be used). The mixture is stirred overnight at room temperature for dissolution. Operating inside a laminar flow hood, the dissolved thermal gel solution was filtered through a 0.2 micron filter into the drug pellet to provide the ophthalmic suspension.

Upon ophthalmic application, the suspension gels; thereby keeping the drug substance in contact with the eye.

Example 3: Suspension for Oral Application:

4% w/w (1% to 6%, preferably, 3% to 5% may be used) of the preferred copolymer of the above Second Preparation, is added to a suspension of acetaminophen. The mixture is stirred overnight at room temperature in a sanitized area to provide the suspension for oral application.

Upon oral administration the suspension gels.

Example 4: Solution Preparation from Drug Substances for Ophthalmic Application:

Timolol maleate is used as a model compound.

5% w/v (1% to 6%, preferably 3% to 5% may be used) of the preferred copolymer of the above Second Preparation, and 0.1% w/v benzalkonium chloride is allowed to dissolved in phosphate balance buffer by stirring overnight at room temperature. Timolol maleate at a concentration of 6.8 mg/ml is dissolved into the preferred copolymer/ benzalkonium chloride. The solution is then sterile filtered through a 0.2 micron filter aseptically before use.

Upon ophthalmic administration the solution gels.

Example 5: Solution Preparation from Drug Substance for Nasal Application:

Phenylephrine hydrochloride is used as a model compound.

3% w/v (however, 1% to 6%, preferably 2% to 4% may be used) of the preferred copolymer of the above Second Preparation, phenylephrine hydrochloride at 0.5% and pheniramine maleate at 0.2% were dissolved in PBS containing 0.4% alcohol and 0.02% benzalkonium chloride.

Upon nasal administration the solution gels.

The invention has been described with particular reference to preferred embodiments thereof, but it will be understood that variations and modifications can be effected within the spirit and scope of the invention.

We claim:

1. A pharmaceutical composition comprised of
   a) a triblock copolymer having the following repeating units in random order $$-((E_sP_rE_r)CH_2O)_z-$$

wherein

P is oxypropylene,

E is oxyethylene, r is an integer from 2 to 160, s is an integer from 15 to 65, and z is an integer from 2 to 50, wherein the triblock copolymer gels at physiological temperature, and b) a therapeutic agent, wherein the therapeutic agent is present as
   (I) nanoparticles of the therapeutic agent having the block copolymer adsorbed on the surface thereof,
   (II) a suspension in a solution of the block copolymer, or
   (III) an aqueous solution in a solution of the block copolymer.

2. A composition according to claim 1 wherein said block copolymer has the following repeating units in random order $$-[(E_sP_rE_r)CH_2O]_z-$$

wherein

P is oxypropylene;

E is oxyethylene;

r is an integer from 75 to 150;

s is an integer from 30 to 50; and, z is an integer from 2 to 10.

3. A composition according to claim 1 wherein said block copolymer has the formula:

$$-[(CH_2CH_2O)_r(CH_2CHO)_s(CH_2CH_2O)_r(CH_2O)]_z-$$
$$\qquad\qquad\qquad\; |$$
$$\qquad\qquad\qquad CH_3$$

wherein r is 114; s is 44 and z is 3 to 4.

4. A composition according to claim 1 wherein said block copolymer has the formula:

$$-[(E_sP_rE_r)CH_2O]_z-[(E_r)CH_2O]_w-$$

wherein

P is oxypropylene;

E is oxyethylene;

r is an integer from 2 to 160;

s is an integer from 15 to 65;

z is an integer from 2 to 50;

t is an integer from 1 to 10; and w is an integer from 2 to 50.

5. A composition according to claim 1 wherein said therapeutic agent is an agent for ophthalmic application.

6. A composition according to claim 1 wherein said therapeutic agent is an agent for nasal application.

7. A composition according to claim 1 wherein said therapeutic agent is an agent for oral application.

* * * * *